US005755712A

United States Patent [19]

Szempruch et al.

[11] Patent Number: 5,755,712
[45] Date of Patent: May 26, 1998

[54] TAMPER EVIDENCE FEATURE FOR STERILE PORT AND CAP SYSTEM

[75] Inventors: Walter T. Szempruch, Gurnee; Victor M. Trentadue, Arlington Heights; Stephen C. Yeaton, Lindenhurst, all of Ill.

[73] Assignee: Abbott Laboratories, Abbott Park, Ill.

[21] Appl. No.: 361,416

[22] Filed: Dec. 22, 1994

[51] Int. Cl.[6] .......... A61B 19/00; A65D 41/10

[52] U.S. Cl. .......... 604/403; 206/807; 215/324; 215/901; 215/DIG. 3

[58] Field of Search .......... 604/403, 405; 215/250, 324, 901, DIG. 3; 206/807

[56] References Cited

U.S. PATENT DOCUMENTS

| | | | |
|---|---|---|---|
| 2,653,609 | 9/1953 | Smith | 604/415 |
| 3,994,412 | 11/1976 | Difiglio . | |
| 4,205,754 | 6/1980 | Nielsen et al. | 215/DIG. 3 |
| 4,619,651 | 10/1986 | Kopfer et al. | 604/415 |
| 4,631,685 | 12/1986 | Peter | 364/476 |
| 4,779,997 | 10/1988 | Schmidt . | |
| 5,334,180 | 8/1994 | Adolf et al. . | |
| 5,573,134 | 11/1996 | Chenault et al. | 215/250 |

*Primary Examiner*—John G. Weiss
*Assistant Examiner*—Dennis Ruhl
*Attorney, Agent, or Firm*—Neal D. Marcus

[57] ABSTRACT

A port and cap assembly for a solution container is provided. The port includes a tubular wall having a first end and second end, the first end securable to the container and the second end being open and opposite to the first end. An annular flange extends perpendicularly outward from the cylindrical wall between the first end and the second end to define a neck portion of the cylindrical wall. A circumferential sleeve extends longitudinally downward from the annular flange. A radial lip extends generally perpendicularly inward from the sleeve. A resilient cap is also provided which includes a first portion resiliently stretched to cover the open end of the port and a second portion removably captured between the annular flange and the radial lip. The second portion of the cap after being removed from between the annular flange and the radial lip is not recapturable between the annular flange and the radial lip so as to indicate that the port has been uncovered. A method for assembling a port and cap to a solution container is also provided.

16 Claims, 2 Drawing Sheets

TAMPER EVIDENCE FEATURE FOR STERILE PORT AND CAP SYSTEM

FIELD OF THE INVENTION

This invention relates to a tamper indicating port and cap assembly for a container. More particularly, this invention relates to a port and non-breakaway cap assembly for a solution container, which resists replacement of the cap on the access port, thereby indicating to the user that the sterility of the access port has been compromised.

BACKGROUND OF THE INVENTION

In the packaging arts, it is often necessary to provide the user with a port through which the contents of the package may be accessed. For example, in the medical field, ports allow a user to access the contents within the container so that they can be infused into a patient, transferred to a second package, or mixed with additional components. To access the contents, a sealed diaphragm, located within the port, must be pierced by a needle or piercing pin. Thus, access ports have an open end for receiving the piercing pin which contacts and pierces the diaphragm.

For intravenous solution containers, it is particularly important that the open end of the access ports remain sterile so as to prevent the transfer of contaminants into the solution by the pin inserted into the port to pierce the diaphragm. To protect the sterility of the access port, current containers employ removable caps which cover the port opening during storage and transportation prior to use. Some port and cap assemblies, such as that described in U.S. Pat. No. 3,994,412, are equipped with caps that are designed to frangibly breakaway from the port. Although breakaway ports provide a clear indication of having been used, they are difficult and complex to manufacture. Alternative, less complex port and cap devices, such as those described in U.S. Pat. Nos. 5,334,180 and 4,779,997 are not breakaway, but rather are equipped caps that are removably secured to the port. U.S. Pat. No. 4,779,997 for example, describes a cap having a guide member, sleeve member and handle member. The guide member, in cooperation with the sleeve member, defines an annular channel that receives a portion of the neck of the port. The annular channel defined by the sleeve and guide members, has a sufficiently small inner circumference so as to fit securely over the port neck. The handle member is provided to assist the user in removing the cap from the port. To remove the cap, the user must overcome the retaining force by applying a pulling force of approximately ten pounds to the handle.

The major disadvantages of a non-breakaway cap and port assemblies such as the device of U.S. Pat. No. 4,779,997 is that once the caps are removed, the ports do not provide an effective deterrent to replacement of the caps nor do they provide a user with an indication that the caps have been previously removed and replaced. Thus, a user may be unaware if the sterility of the port has been compromised.

Thus it is desirable to provide a novel port and cap assembly that provides a deterrent to cap replacement. It is also desirable to provide a port and cap assembly that provides the user with a quick and clear indication that the cap has been previously removed. In this way the user is made aware that the sterile open end of the port may be compromised.

SUMMARY OF THE INVENTION

The present invention relates to a port and cap assembly for a solution container. A tubular port is provided including a cylindrical wall having a first end and second end, the first end securable to the container and the second end being open and opposite to the first end. An annular flange extends perpendicularly outward from the cylindrical wall between the first end and the second end to define a neck portion of the cylindrical wall in a direction away from the first end. A circumferential sleeve extends longitudinally from the annular flange in the direction away from the first end. A radial lip extends generally perpendicularly inward from the sleeve. A resilient cap is also provided which includes a first portion resiliently stretched to cover the open end of the port and a second portion removably captured between the annular flange and the radial lip. The second portion of the resilient cap after being resiliently removed from between the annular flange and the radial lip is not recapturable between the annular flange and the radial lip without further manipulation of the annular flange and radial lip, so as to indicate that the port has been uncovered.

The present invention is also directed to a method for assembling a port and cap to a solution container including the steps of:

a. providing a tubular port having a cylindrical wall including a first end and a second open end, an annular flange extending perpendicularly outward from the cylindrical wall between the first end and the second open end and a sleeve extending longitudinally downward from the annular flange in the direction away from the first end;

b. providing a resilient cap including a first portion for covering the open end of the port and a second portion for abutting the annular flange;

c. seating the cap on the port so that the first portion of the resilient cap resiliently stretches and covers the open end and the second portion abuts the annular flange;

d. bending a portion of the sleeve radially inward to form a generally radial lip to removably capture the second portion of the resilient cap between the annular flange and the radial lip wherein the second portion after being resiliently removed is not recapturable between the annular flange and the radial lip so as to indicate that the port has been uncovered. In the preferred embodiment, the bending step is accomplished by applying ultrasonic energy to the circumferential sleeve.

DESCRIPTION OF THE PREFERRED EMBODIMENT

Figure 1:
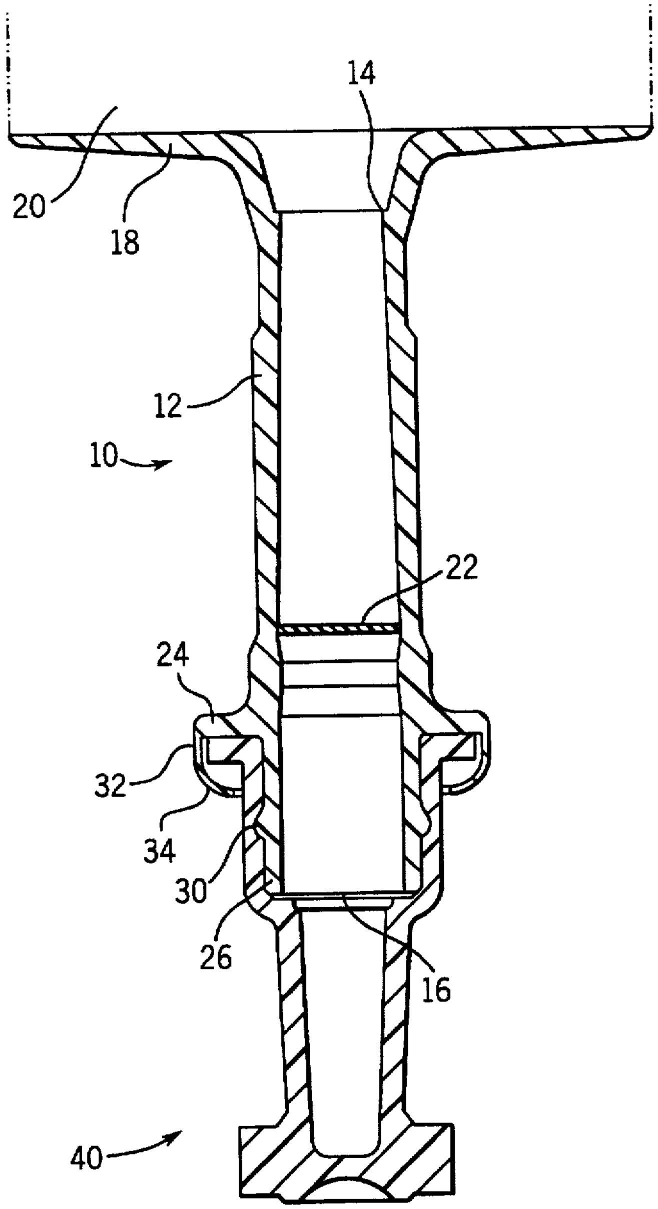
FIG. 1 is a front vertical section view of the port and cap assembly of the present invention.
Figure 2:
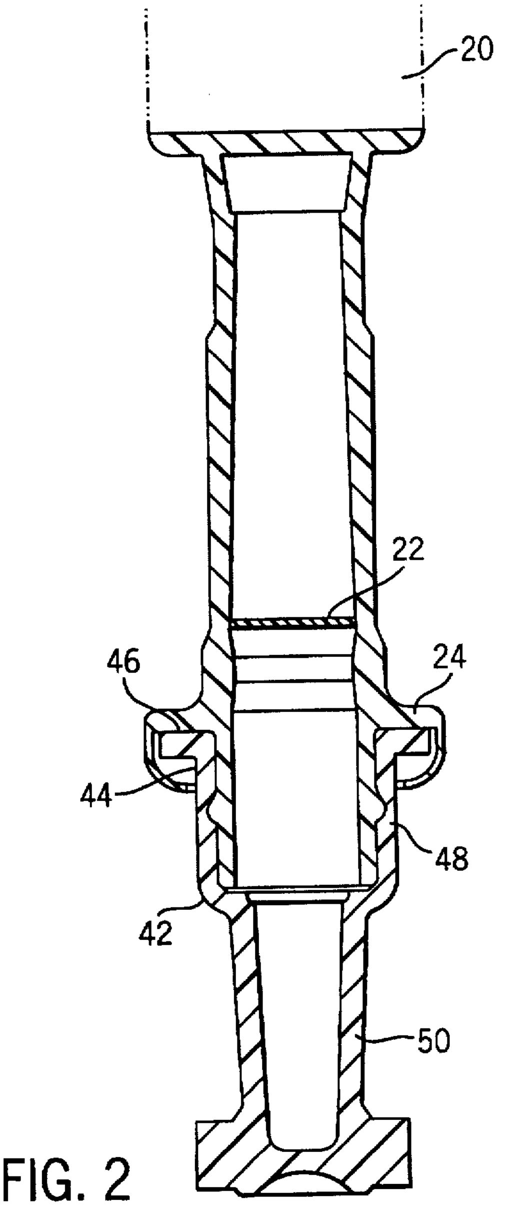
FIG. 2 is a side vertical section view of the same port and cap assembly as shown in FIG. 1.

Referring now to the drawings, a detailed description of the port and cap assembly follows. As seen in FIGS. 1 and 2, the tubular port (10) includes a cylindrical wall (12) having a first end (14) and a second end (16). The cylindrical wall (12) of the port (10) is preferably molded of a semi-rigid medical grade plastic. The first end (14) may include a container flange (18) that is bondable by heat, adhesive or radio frequency bonding for example, to the plastic material of the container (20) so as to secure the tubular port (10) to the container. The manner of attachment of the first end (14) of the port assembly to the container (20) is not important to the operation of the present invention.

The port and cap assembly of the present invention is suitable for use with most containers having a piercable diaphragm located within the port for sealing the port from the container. An example of such a tubular port and diaphragm is described in U.S. Pat. No. 5,334,180 entitled "Sterile Formed, Filled and Sealed Flexible Container" the disclosure of which is herein incorporated by reference in this application.

The cylindrical wall also includes a second end (16) that is open and opposite to the first end (14). Open means that the piercable diaphragm (22) of the port is located at a position in the port other than immediately at the second end (16). An annular flange (24) extends perpendicularly outward from the cylindrical wall (12) at a location on the cylindrical wall between the first end (14) and the second open end (16). The annular flange (24) defines a neck portion (26) of the cylindrical wall (12). The neck portion (26) extends in the direction away from the first end (14). Accordingly, the length of the neck portion (26) is determined by the position of the annular flange (24) along the cylindrical wall (12) relative to the second end (16).

The neck portion (26) of the cylindrical wall (12) further includes at least one annular outward projection (30) that provides a ring of increased diameter relative to the outer surface of the neck portion (26) which lacks this feature. The annular outward projection (30) serves to increase the resilient stretch necessary for the cylindrical portion (48) of the resilient cap (40) to cover the neck portion (26) of the port (10), which will be described below.

A thin circumferential sleeve (32) extends longitudinally downward from the annular flange (24). The circumferential sleeve (32) is concentrically outward from the neck portion (26) of the cylindrical wall and also extends in the direction away from the first end (14). In the final assembled position, the end portion of the thin sleeve is bent inward to form a radial lip (34) that extends generally perpendicularly inward from the unbent portion of the circumferential sleeve (32). The radial lip (34) is longitudinally spaced from and parallel to the annular flange (24).

The longitudinal cylindrical wall (12), the annular outward flange (24), the longitudinal downward sleeve (32) and the radial inward lip (34) are preferably made of a moldable plastic material by an injection mold process. That is, these structures are preferably molded as an integral unit of the same material. Suitable plastic materials include semi-rigid or rigid thermoplastics such as low density polyethylene or unplasticized polyvinylchloride (PVC).

Also seen in FIGS. 1 and 2, is a generally cylindrical cap (40) made of a resilient elastomeric material which includes a first portion (42) covering the open end (16) of the port (10) and a second portion (44). The second portion (44) includes an outward radial flange (46) removably captured in the space between the parallel annular flange (24) and the parallel radial lip (34) of the port (10). Since the cap (40) is made of a resilient elastomeric material, the outward radial flange (46) can be stretched so as to be disengagable from the captured position. Preferably, the cap (40) is constructed from a commercially available synthetic rubber such as ethylene propylene dienemonomer (EPDM) rubber. The first portion (42) of the cap (40) has a closed end and includes a cylindrical portion (48) for covering the neck portion (26) of the port (10). Preferably, the inner diameter of the cylindrical portion (48) of the cap (40) is less than the outer diameter of the neck portion (26) of the port (10). Thus, the inner diameter of the cylindrical portion (48) of the cap (40) is also less than the outer diameter of the outward ring projection (30). The diameter of the cylindrical portion (48) of the cap (40) should be smaller than the diameter of the neck portion (26) of the tubular port (10) so as to require the application of approximately 10 to 20 pounds of force in order to remove the resilient cap (40) from the outward projection (30) on the neck portion (26) of the port (10). The cap (40) also includes a stem portion (50) axially extending from the closed end of the cap (40) to facilitate grasping by the user's hand for manual removal of the outward radial flange (46) of the cap (40) from between the annular flange (24) and radial lip (34) of the port (10).

Figure 3:
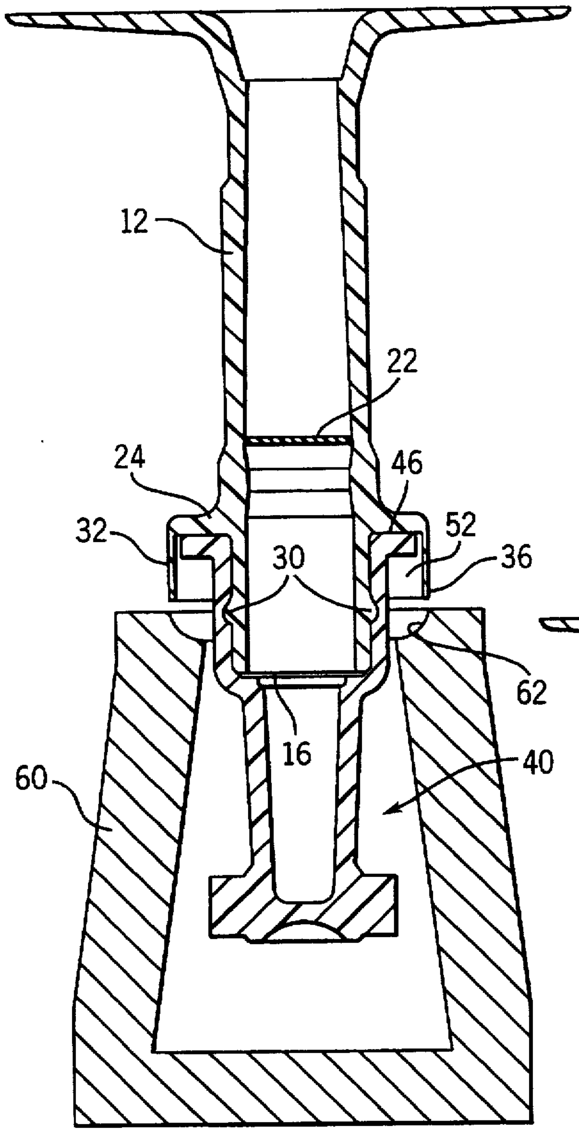
FIG. 3 is a front vertical section view showing the sleeve of the port and cap assembly of FIG. 1 in a pre-formed state.
Figure 4:
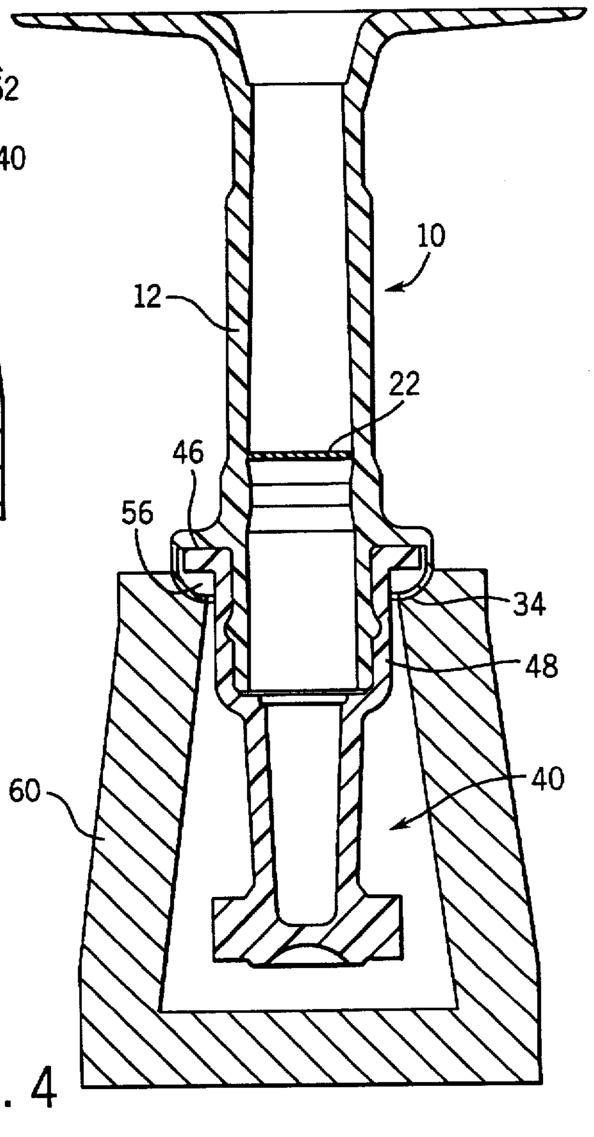
FIG. 4 is a front vertical section view showing part of the sleeve being formed into a radial lip.

A better understanding of the advantages of the port and cap assembly will be gained by a description of their fabrication. FIG. 3 shows the port and cap assembly prior to capture of the outward radial flange of the cap. During the initial assembly of the port (10), the sleeve (32) extends concentrically with and in the same direction as the cylindrical wall (12) of the tubular port, to allow placement of the cap (40) on the neck portion (26) of the port (10). Initially the sleeve (32) is of sufficient length to provide a suitable portion that can be bent to form a radial lip (34) as will be described below. The cap (40) is inserted onto the neck portion (26) of the port by applying either constant or intermittent pressure to the outward radial flange (46) of the cap (40), until the first portion (42) of the cap (40) stretches and covers both the open end (16) and essentially the entire cylindrical neck portion (26) of the port (10). By this process, the outward radial flange (46) of the cap (40) is positioned within the channel (52) defined by the neck portion (26), the annular flange (24) and the sleeve (32) of the port (10). Preferably, the outward radial flange (46) of the cap (40) is adjacent or nearly abuts the annular flange (24) of the port. A small radial clearance is left between the outer edge of the outward radial flange (46) of the cap (40) and the inner surface of the sleeve (32).

To produce the tamper indicating feature of the present invention, energy such as heat or ultrasonic is applied to the end portion (36) of the plastic sleeve (32) causing the tip (36) to permanently bend or curve in an inward, generally perpendicular direction, to form a generally radial lip (34). The energy applied may be either sonic energy or thermal energy. For either energy applied, it is also necessary to apply physical forming pressure to the heated sleeve (32) to effect formation of the radial lip (34). The forming step is accomplished by applying thermal or sonic energy and pressure, the amount of which depends both on the type of plastic material used to manufacture the tubular port and on the dimensions of the thin circumferential sleeve. That is, certain plastic materials may require higher energies and/or greater forming pressure to effect formation of the radial lip, but such parameters are known to one of ordinary skill in the art.

In a preferred embodiment, the tip of the sleeve (36) is contacted with a sonic horn (60) and ultrasonic energy in the range of about 20 to about 40 kilohertz (Khz) is applied. The sonic horn gradually descends and folds over the end portion of the sleeve (32) in the general direction parallel to the annular flange (24). As the sleeve is vibrated by ultrasonic energy, the plastic of the sleeve (32) becomes molten. The sleeve (32) then assumes the shape or contour of the sonic horn at the contact forming surfaces (62) between the sleeve (32) and the horn (60). The ultimate displacement of the sonic horn along the sleeve determines how much of the sleeve (32) becomes bent or curved, thereby defining the final inward extent of the radial lip (34).

In the preferred embodiment, sufficient energy is applied to form a radial lip (34), that in cooperation with the parallel annular flange (24) encloses (i.e. captures) the radial flange (46) of the resilient cap (40). Furthermore, the unbent portion of the sleeve (32) is of sufficient length to provide an interstitial space (56) between the radial lip (34) and the surface of the radial flange (46) of the cap (40) facing the radial lip (34). The only limitation to the formation of the radial lip (34) is the preference that the radial lip not touch nor bond anywhere to the radial flange (46) of the resilient cap (40).

It is understood that the final inward dimension of the radial lip (34) depends on multiple factors such as the initial length of the sleeve (32), the size of the outward radial flange (46) of the cap and the extent to which the outward radial flange (46) of the cap is desired to be enclosed. Determination of such parameters however, is known to one of ordinary skill in the art. Once completed, the port and cap assembly may be attached to a suitable solution container by a suitable connecting process known in the art.

To remove the resilient cap for purposes of penetrating the diaphragm (22) and obtaining access to the contents of the container, the user grasps the stem (50) of the cap and applies an axial pulling force in the range of about 10 to about 20 pounds. The outward radial flange (46) of the resilient cap, stretches easily when pulled from the captured position whereas the annular flange (24) and radial lip (34) of the port (10) remain essentially undistorted. Once the resilient cap (40) has been removed from the port, a user trying to replace the cap would find it difficult to recapture the outward radial flange (46) of the cap between the radial lip (34) and annular flange (24) of the port. The radial lip (34) deters the replacement of the cap (40) to the original captured position without making the initial manufacture or assembly unduly complex. A partially replaced cap (40) would indicate to the next user that the cap had been removed at least once. In this way, the user is made aware that the sterile open end of the port has been uncovered.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

We claim:

1. An assembly for a solution container including a tubular port and a resilient cap, said tubular port comprising:

a cylindrical wall having a first end and second end, said first end securable to said container and said second end being open and opposite to said first end;

an annular flange extending from said cylindrical wall between said first end and said second end, said cylindrical wall having a neck portion extending from said flange to said second end, said flange being non-frangible and made of material of sufficient rigidity to maintain its shape when said cap is removed from said port;

a circumferential sleeve extending longitudinally form said annular flange in the direction away from said first end toward said second end; and a radial lip extending generally perpendicularly inward from said sleeve, said resilient cap including a first portion resiliently stretched to cover said open end of said port and a second portion removably captured between said annular flange and said radial lip, whereby said second portion of said resilient cap after being resiliently removed from between said annular flange an said radial lip is not recapturable between said annular flange and said radial lip without manipulation of said non-frangible annular flange and said radial lip, so as to indicate that said port has been uncovered.

2. The assembly of claim 1 further including a stem portion axially extending from said first portion of said cap to facilitate manual removal of said second portion of said cap from between said annular flange and said radial lip.

3. The assembly of claim 1 wherein said first portion of said cap includes a cylindrical portion for covering said neck portion and said second portion includes an outward radial flange.

4. The assembly of claim 3 wherein said neck portion includes an outer diameter larger than the inner diameter of said cylindrical portion of said resilient cap.

5. The assembly of claim 4 wherein said neck portion further includes an outward annular ring to increase the resilient stretch necessary for said cylindrical portion or said resilient cap to cover said neck portion of said port.

6. A method for assembling a port and cap to a solution container comprising the steps of:

a. providing a tubular port having a cylindrical wall including a first end and a second open end, an annular flange extending perpendicularly outward from said cylindrical wall between said first end and said second open end and a sleeve extending longitudinally downward from said annular flange in the direction away from said first end, said annular flange being non-frangible and formed of a material of sufficient rigidity to maintain its shape when said cap is removed;

b. providing a resilient cap including a first portion for covering said open end of said port and a second portion for abutting said annular flange;

c. seating said cap on said port so that said first portion of said resilient cap resiliently stretches and covers said open end and said second portion abuts said annular flange;

d. bending a portion of said sleeve radially inward to form a generally radial lip to removably capture said second portion of said resilient cap between said annular flange and said radial lip whereby said second portion after being resiliently removed is not recapturable between said non-frangible annular flange and said radial lip without further manipulation of said annular flange and radial lip so as to indicate that said port has been uncovered.

7. The method of claim 6 wherein said sleeve is made of a thermal deformable material and said bending step is accomplished by applying heat to said circumferential sleeve.

8. The method of claim 6 wherein said bending step is accomplished by applying ultrasonic energy to said circumferential sleeve.

9. The method of claim 7 wherein said thermal deformable material is plastic.

10. The method of claim 9 wherein said plastic is low density polyethylene.

11. The assembly of claim 1 wherein said sleeve, radial lip and cap define a space for receiving the second portion of the resilient cap.

12. An assembly for a solution container including a tubular port and a resilient cap, said tubular port comprising:

a cylindrical wall having a first end and second end, said first end securable to said container and said second end being open and opposite to said first end;

an annular flange extending perpendicularly from said cylindrical wall between the first end and said second end, said cylindrical wall having a neck portion extending from said flange to said second end;

a circumferential sleeve extending longitudinally from said annular flange in the direction away from said first end toward said second end; and a radial lip extending generally perpendicularly inward from said sleeve, said resilient cap including a first portion resiliently stretched to cover said open end of said port and a second portion removably captured between said annular flange and said radial lip, whereby said second portion of said resilient cap after being resiliently removed from between said annular flange and said radial lip is not recapturable between said annular flange and said radial lip without manipulation of said annular flange and said radial lip, so as to indicate that said port has been uncovered, said assembly further including a stem portion axially extending from said first portion of said cap to facilitate manual removal of said second portion of said cap from between said annular flange and said radial lip.

13. A port and cap assembly for a solution container including a tubular port and a resilient cap, said tubular port comprising:

a cylindrical wall having a first end and second end, said first end securable to said container and said second end being open and opposite to said first end;

an annular flange extending perpendicularly from said cylindrical wall between said first end and said second end, said cylindrical wall having a neck portion extending from said flange to said second end;

a circumferential sleeve extending longitudinally from said annular flange in the direction away from said first end; and a radial lip extending generally perpendicularly inward from said sleeve, said resilient cap including a first portion resiliently stretched to cover said open end of said port and a second portion removably captured between said annular flange and said radial lip, whereby said second portion of said resilient cap after being resiliently removed from between said annular flange and said radial lip is not recapturable between said annular flange and said radial lip without manipulation of said annular flange and said radial lip, so as to indicate that said port has been uncovered, said first portion of said cap includes a cylindrical portion for covering said neck portion and said second portion includes an outward radial flange.

14. The assembly of claim 13 wherein said neck portion has an outer diameter larger than the inner diameter of said cylindrical portion of said resilient cap.

15. The assembly of claim 14 wherein said neck portion includes an outward annular ring to increase the resilient stretch necessary for said cylindrical portion or said resilient cap to cover said neck portion of said port.

16. A port and cap assembly for a solution container including a tubular port and a resilient cap, said tubular port comprising:

a cylindrical wall having a first end and second end, said first end securable to said container and said second end being open and opposite to said first end;

an annular flange extending from said cylindrical wall between said first end and said second end, said cylindrical wall having a neck portion extending from said flange to said second end, said flange being non-frangible and made of material of sufficient rigidity to maintain its shape when said cap is removed from said port;

a circumferential sleeve extending longitudinally from said annular flange in the direction away from said first end toward said second end; and a radial lip extending generally perpendicularly inward from said sleeve, said resilient cap including a first means resiliently stretched over said open end of said port for covering said end and second means removably captured between said annular flange and said radial lip for engaging said flange, whereby said second means of said resilient cap after being resiliently removed from between said annular flange and said radial lip is virtually not recaptured between said annular flange and said radial lip without manipulation of said non-frangible annular flange and said radial lip, so as to indicate that said port has been uncovered.

* * * * *